United States Patent [19]

Rocco

[11] Patent Number: 4,958,623
[45] Date of Patent: Sep. 25, 1990

[54] PROTECTIVE DEVICE FOR ENDOSCOPISTS, IN PARTICULAR FOR URETHRAL USE

[76] Inventor: Francesco Rocco, Via Fogazzaro, 20, 20135 Milan, Italy

[21] Appl. No.: 419,034

[22] Filed: Oct. 10, 1989

[30] Foreign Application Priority Data

Oct. 24, 1988 [IT] Italy ................. 22054/88[U]

[51] Int. Cl.⁵ .............................................. A61B 1/00
[52] U.S. Cl. ........................................ 128/7; 128/4; 128/857
[58] Field of Search ............... 128/4, 6, 7; 606/46

[56] References Cited

U.S. PATENT DOCUMENTS

| 1,662,227 | 3/1928 | Allyn | 128/7 |
| 1,679,950 | 8/1928 | Stern | 606/46 |
| 4,834,068 | 5/1989 | Gottesman | 128/4 |
| 4,848,322 | 7/1989 | Dash et al. | 128/4 |

Primary Examiner—William H. Grieb
Attorney, Agent, or Firm—Bucknam and Archer

[57] ABSTRACT

There is disclosed a protective device for endoscopists, in particular for urethral use, which comprises a plate-like screen, which can be arranged so as to encompass the eye-piece associated with the optical detecting element, to be introduced into the catheter, in order to display the operating field.

2 Claims, 2 Drawing Sheets

PROTECTIVE DEVICE FOR ENDOSCOPISTS, IN PARTICULAR FOR URETHRAL USE

BACKGROUND OF THE INVENTION

The present invention relates to a protective device for endoscopists, which has been specifically designed for an urethral type of use.

As is known, for examining urethral members by means of an endoscope, the physician must insert a catheter or rigid or flexible sleeve into the urethral duct and apply an eye-piece, coupled to optical fibres or optical devices, sliding within the inside of the catheter and adapted to visually reproduce on outside tools the operating inner field of the patient.

During such an operation, possible tightness losses can occur, at the catheter, thereby the physician is frequently impacted, on his face, by urine, blood or other liquid sprays as ejected from the urethral duct.

This fact, in addition to originating great sanitary problems, causes difficult to properly perform the endoscopy operation, since the field of view of the physician is negatively affected.

SUMMARY OF THE INVENTION

Thus, the aim of the present invention is to overcome the above mentioned drawbacks, by making a protective device for endoscopists, which has been specifically designed for urethral use, and which is adapted to properly protect the physician during the endoscopy operation, while remarkably improving the sanitary operative conditions.

Within the scope of the above mentioned aim, a main object of the present invention is to provide such a protective device which allows for the physician to operate in a quicker and safer way and which, moreover, is very reliable in operation and can be applied in a very simple and quick way to conventional endoscopes.

According to one aspect of the present invention, the above mentioned aim and objects, as well as yet other objects, which will become more apparent hereinafter, are achieved by a protective device for endoscopists, specifically designed for urethral use, characterized in that said protective device comprises a plate-like screen which can be applied about an eye-piece associated with an optical detecting element provided for insertion into a catheter in order to display an operating field.

BRIEF DESCRIPTION OF THE DRAWINGS

Further characteristics and advantages of the invention will become more apparent from the following detailed description of a preferred, though not exclusive, embodiment of a protective device for endoscopists, specifically designed for urethral use, which is illustrated, by way of an indicative but not limitative example, in the accompanying drawing, where.

DESCRIPTION OF THE PREFERRED EMBODIMENT

Figure 1:
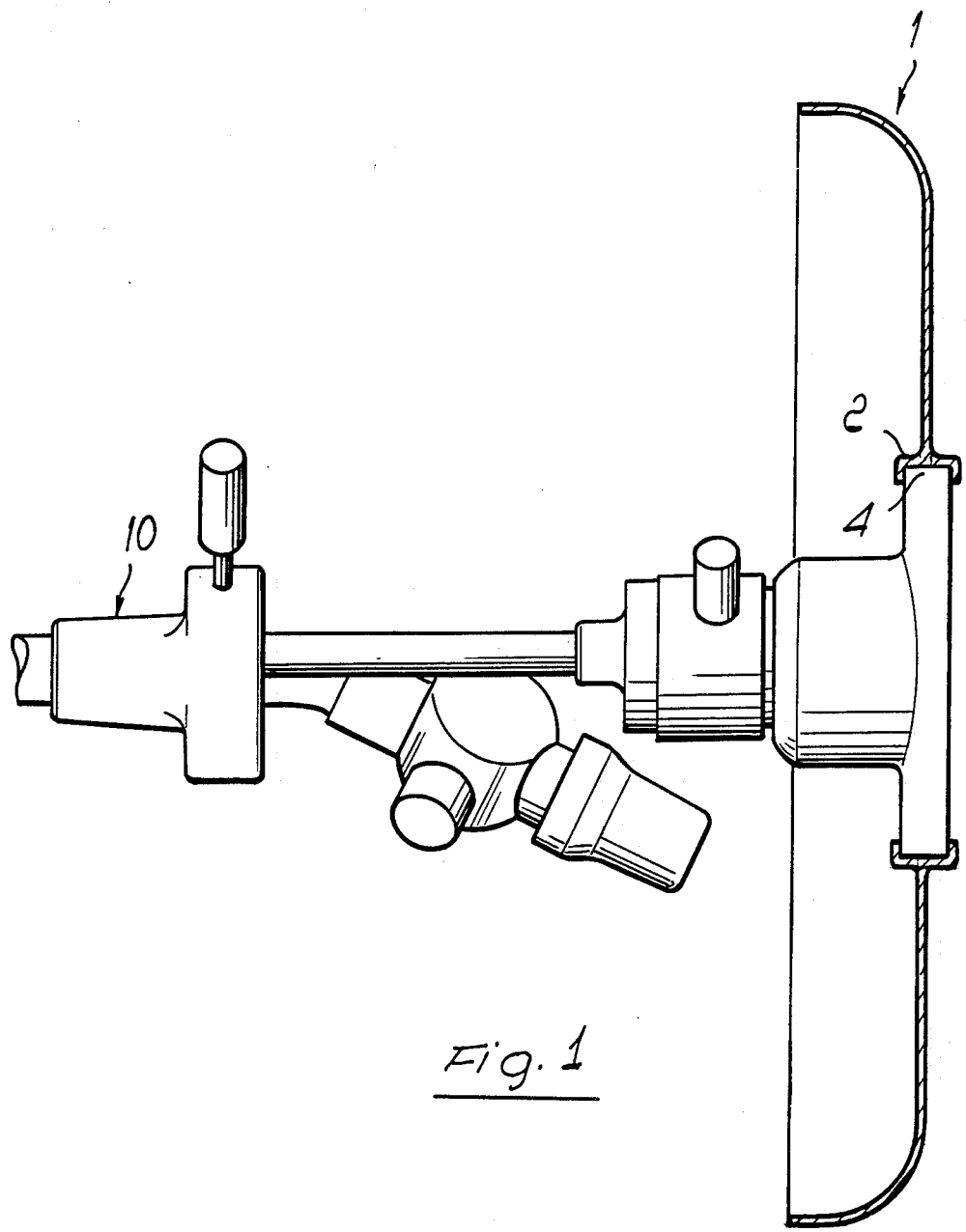
FIG. 1 is a schematic view illustrating the subject protective device applied to a catheter.
Figure 2:
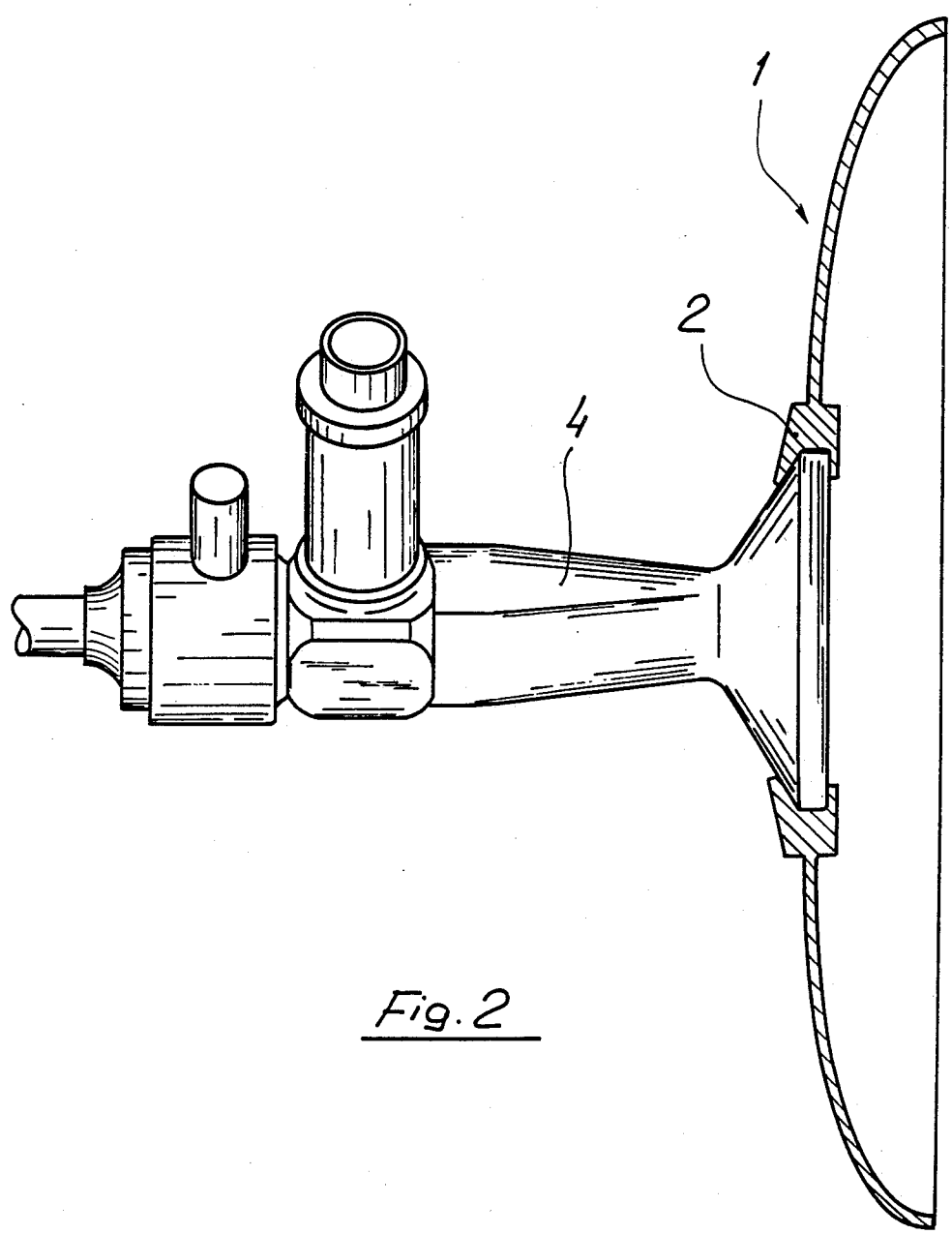
FIG. 2 clearly shows the coupling between an eyepiece and the protective device according to the present invention.

With reference to the figures of the accompanying drawings, the protective device for endoscopists, specifically designed for urethral use, according to the invention, comprises a plate-like screen, indicated at the reference number 1, which has a preferably disc-like configuration, and includes edge portions which can have their concavity or curved edge facing either one or the other side, as it will become more apparent hereinafter.

At its central portion, the plate-like element 1 comprises a resiliently yieldable ring member 2, which can be removably engaged about an eye-piece 4 associated with an optical detecting element, which generally comprises optical fibres, and which can be introduced slidingly into the catheter 10 so as to easily provide a display of the patient operating field. In particular, the ring member 2 has an inverted-U cross-section firmly engaging with the periphery of the eye-piece 4 so that, in its engaged condition, the plate screen 1 can not axially move with respect to the eye-piece 4 and catheter 10.

More specifically, the mentioned plate-like element can be preferably, though not necessarily, made of an optically transparent material, so as to provide perfect viewing characteristics for the physician, while holding the desired protective properties.

As stated, at its edge portions, the disc shaped element forming the protective screen, can have its concavity or curved edge facing the operating field, thereby operating as a repulsione member for a possible urine spray, or, if desired, it can be arranged with its concavity or curved edge facing the physician, so as to provide a protective element for the physician.

A main feature of the subject device is that it can be easily fitted to conventional endoscopy implements, without the need of modifying these implements, since the device according to the invention comprises a resilient ring member allowing for said device to be directly applied on the eye-piece of the optical instrument.

From the above disclosure it should be apparent that the present invention fully achieves the intended aim and objects.

In particular, a very efficient protective device has been provided which is very reliable in operation and can be quickly and easily applied to conventional endoscopy implements.

While the invention has been disclosed and illustrated with reference to a preferred embodiment thereof, it should be apparent that the disclosed embodiment is susceptible to several modifications and variations, all of which will come within the spirit and scope of the appended claims.

I claim:

1. A protective device for endoscopists, specifically designed for urethral use, comprising a disc-shaped plate-like screen to be applied about an eye-piece of an optical detecting device to be inserted into a catheter to display a patient operating field, wherein said screen is provided with a curved peripheral edge defining a peripheral concave portion of said screen and with a central resiliently yieldable ring member having a substantially reversed-U cross-section, said ring member being adapted to be engaged with a peripheral portion of said eye-piece so as to prevent said screen from axially moving.

2. A device according to claim 1, wherein said ring member is so designed and arranged that said screen can be removably engaged with said eye-piece with said peripheral concave portion of said screen either facing said operating field, so as to operate as a repulsion member for liquid sprays, or facing and endoscopist so as to provide a protective member of said endoscopist.

* * * * *